United States Patent
Gankkhanov et al.

(10) Patent No.: US 7,616,304 B2
(45) Date of Patent: Nov. 10, 2009

(54) SYSTEM AND METHOD FOR PROVIDING A TUNABLE OPTICAL PARAMETRIC OSCILLATOR LASER SYSTEM THAT PROVIDES DUAL FREQUENCY OUTPUT FOR NON-LINEAR VIBRATIONAL SPECTROSCOPY AND MICROSCOPY

(75) Inventors: Feruz Gankkhanov, Annandale, NJ (US); Silvia Carrasco, Castelldefels (ES); Xiaoliang Sunney Xie, Lexington, MA (US)

(73) Assignee: President & Fellows of Harvard College, Cambridge, MA (US)

( * ) Notice: Subject to any disclaimer, the term of this patent is extended or adjusted under 35 U.S.C. 154(b) by 0 days.

(21) Appl. No.: 11/778,838

(22) Filed: Jul. 17, 2007

(65) Prior Publication Data

US 2008/0037595 A1    Feb. 14, 2008

Related U.S. Application Data

(63) Continuation of application No. PCT/US2006/001736, filed on Jan. 19, 2006.

(60) Provisional application No. 60/645,890, filed on Jan. 21, 2005.

(51) Int. Cl.
*G01J 3/44* (2006.01)

(52) U.S. Cl. .................................. 356/301

(58) Field of Classification Search .................. 356/301
See application file for complete search history.

(56) References Cited

U.S. PATENT DOCUMENTS

| 5,377,219 | A |   | 12/1994 | Geiger |
| 5,619,517 | A |   | 4/1997  | Dixon |
| 5,841,570 | A |   | 11/1998 | Velsko |
| 5,999,547 | A | * | 12/1999 | Schneider et al. ........... 359/330 |
| 6,683,894 | B1 |  | 1/2004  | Lee et al. |
| 2001/0028460 | A1 | * | 10/2001 | Maris et al. ................. 356/432 |
| 2003/0007145 | A1 |   | 1/2003  | Shimada |
| 2005/0110990 | A1 | * | 5/2005  | Koo et al. .................... 356/301 |
| 2005/0206904 | A1 | * | 9/2005  | Zaugg ......................... 356/451 |
| 2005/0243324 | A1 | * | 11/2005 | Freeling et al. ............. 356/450 |

OTHER PUBLICATIONS

Powers et al., "Recent advances of the Ti: sapphire-pumped high-repitition-rate femtosecond optical parametric oscillator" J. Optical Society of America, Nov. 1993, vol. 10, No. 11, pp. 2162-2167.

(Continued)

*Primary Examiner*—Kara E Geisel
(74) *Attorney, Agent, or Firm*—Gauthier & Connors LLP (57) ABSTRACT

A system is disclosed for providing a first electromagnetic field and a second electromagnetic field to vibrational analysis equipment that is responsive to a difference between first and second frequencies of the first and second electromagnetic fields respectively. The system includes a non-linear crystal that may be pumped at a high repetition rate to provide a pulsed signal field at a signal field frequency and a pulsed idler field at an idler field frequency as output. The signal field provides the first electromagnetic field and the idler field provides the second electromagnetic field. The system also includes a tuning system for permitting the difference between the signal field frequency and the idler field frequency to be changed. The system also includes an output unit for providing the first and second electromagnetic fields to the vibrational analysis equipment.

24 Claims, 8 Drawing Sheets

OTHER PUBLICATIONS

Batchko et al., "Continuous-wave 532 nm-pumped singly resonant optical parametric oscillator based on periodically poled lithium niobate" Optics Letters, Feb. 1998, vol. 23, No. 3, pp. 168-170.

Heinz et al., "Piosecond Nd: YLF laser-multipass amplifier source pumped by pulsed diodes for the operation of powerful OPOs" Optics Communications, Apr. 1997, pp. 433-436.

Potma et al., "CARS Microscopy for Biology and Medicine" Optical Society of America, Optics and Photonics News, Nov. 2004, pp. 61-63.

Kartaloglu et al., "Femtosecond optical parametric oscillator based on periodically poled KTiOPO4" Jan. 1998, vol. 23 No. 1, 1998 Optical Society of America, pp. 61-63.

* cited by examiner

SYSTEM AND METHOD FOR PROVIDING A TUNABLE OPTICAL PARAMETRIC OSCILLATOR LASER SYSTEM THAT PROVIDES DUAL FREQUENCY OUTPUT FOR NON-LINEAR VIBRATIONAL SPECTROSCOPY AND MICROSCOPY

PRIORITY

This application is a continuation of International Application Serial No. PCT/US2006/001736, filed on Jan. 19, 2006 which claims priority to U.S. Provisional Application No. 60/645,890, filed Jan. 21, 2005, both of which are incorporated herein by reference in their entirety.

Development of the present invention was sponsored, in part, by Grant No. R01 GM062536 from the U.S. National Institute of Health, by Grant No. DB1 0138028 from the U.S. National Science Foundation, and by the U.S. State Department under the Fulbright Program together with the Spanish Ministry of Education and Science. The government has certain rights to this invention.

BACKGROUND

The invention generally relates to laser sources, and particularly relates to laser sources for providing dual frequency outputs fields for applications such as coherent anti-Stokes Raman scattering microscopy (CARS).

CARS microscopy allows imaging of chemical and biological samples by using molecular vibrations as a contrast mechanism. Conventional CARS microscopy is a third order non-linear process and uses two laser fields: a pump electromagnetic field with a center frequency at $\omega_p$ and a Stokes electromagnetic field with a center frequency at $\omega_s$. The pump and Stokes fields interact with a sample and generate a coherent anti-Stokes field having a frequency of $\omega_{AS}=2\omega_p-\omega_s$. When the Raman shift of $\omega_p-\omega_s$ is tuned to be resonant at a given vibrational mode, an enhanced CARS signal is observed at the anti-Stokes frequency $\omega_{AS}$. For example, U.S. Pat. Nos. 6,809,814 and 6,798,507 (the disclosures of which are hereby incorporated by reference) disclose CARS microscopy systems employing epi-detected CARS signals and polarization CARS signals respectively.

Conventional laser sources for CARS microscopy provide broad tuning ranges using, for example, two mode-locked titanium sapphire (Ti:Sapphire) lasers that are electronically synchronized. Although such electronically locked sources provide broad tuning ranges, high spectral resolution, and could function in an ultra short pulse regime for a variety of applications, such sources also exhibit timing jitter due to difficulties of electronic synchronization, and are characterized as being relatively complex and expensive.

Another conventional laser source for CARS microscopy involves a mode-locked Nd:YVO4 pump laser (1064 nm) and a synchronously pumped optical parametric oscillator (OPO), which provides high spectral resolution (about 1 cm$^{-1}$) and has no timing jitter. The OPO is intra-cavity doubled to provide a pump beam for CARS microscopy. A small fraction of the Nd:YVO4 laser provides the Stokes beam. Such laser sources, however, involve narrow tuning ranges that may include gaps, multiple crystals are sometimes required to cover the entire Raman spectral range, the spatial mode quality may be less than is desired because of the intra-cavity doubling, and the pump and stokes wavelengths may be less than desired.

It is desirable to provide a laser source for CARS microscopy that provides continuous tunability for regions of Raman frequencies (e.g., from 500 cm$^{-1}$ to 3500 cm$^{-1}$ which covers most of the resonances in certain applications such as life tissue in biological and molecular applications. Other desirable characteristics include high spectral resolution with wavelength of only a few cm$^{-1}$, low intensity noise (high stability), very good synchronization of the pump and Stokes pulses—high repetition rate for high frame rate imaging, and favorable wavelengths to avoid or reduce photo-damage and to attain higher penetration depths. The system, therefore, provides greater flexibility and functionality for CARS in that operating wavelengths may vary from 900-1300 nm in certain systems of the invention. This significantly impacts capabilities of the system, including penetration depth and non-invasiveness for cells and optically dense soft tissue. The source should also be compact, easy and reliable to use, and low in cost.

Because CARS is a non-linear analytical process for biological applications, high peak power with low average power is required to generate the required signal without degrading the biological sample. Picosecond or femtosecond pulses at high power are therefore desired. U.S. Pat. No. 5,017,806 discloses a synchronously pumped optical parametric oscillator that provides a femtosecond pulse train and is pumped by a femtosecond pulsed dye laser. Although the system is disclosed to be suitable for use with a broad tuning range, dye lasers are considered to be relatively unstable during use and too unreliable over time for use in vibrational biological analyses.

Mode locked titanium:sapphire (Ti:Sa) lasers are also known to be used to pump optical parametric oscillators, but such systems also do not provide an output of a sufficiently broad spectral range that may cover the entire spectral range for vibrational analysis of biological samples. See for example, P. E. Powers, R. J. Ellington and W. S. Pelouch, *Recent Advances of the Ti:sapphire-pumped high-repetition-rate femtosecond optical parametric oscillator*, J. Opt. Soc. Am., vol. 10, No. 11, November 1998.

It is also known that a non-linear crystal pumped by a continuous wavelength (CW) laser at a frequency in the visible range (about 400-about 700 nm) may be provided using a solid state laser. See for example, R. G. Batchko, D. R. Weise, T. Plettner, G. D. Miller, M. M. Fejer, and R. L. Byer, *Continuous-wave 532-nm-Pumped Singly Resonant Optical Parametric Oscillator Based on Periodically Poled Lithium Niobate*, Optics Letters, Vol. 23, No. 3 (Feb. 1, 1998). Such as system, however, provides a CW signal that is much too high in average power to be used for vibrational biological analyses. Optical parametric oscillators synchronously pumped by picosecond Nd:YLF lasers at frequencies in the visible range have also been reported. See for example, P. Heinz, A. Seilmeier and A. Piskarskas, *Picosecond Nd:YLF laser-multipass amplifier source pumped by pulsed diodes for the operation of powerful OPOs*, Optics Communications, v. 136, pp. 433-436 (1997). The low repetition rates of these systems, however, are not suitable for vibrational biological analysis.

There is a need, therefore, for a more efficient and economical system for providing illumination in a vibrational biological analysis system such as a CARS microscopy or spectroscopy system.

SUMMARY

In accordance with an embodiment, the invention provides a system for providing a first electromagnetic field and a second electromagnetic field to vibrational analysis equipment that is responsive to a difference between first and second frequencies of the first and second electromagnetic fields respectively. The system includes a non-linear crystal that may be pumped at a high repetition rate to provide a pulsed signal field at a signal field frequency and a pulsed idler field at an idler field frequency as output. The signal field provides the first electromagnetic field and the idler field provides the second electromagnetic field. The system also includes a tuning system for permitting the difference between the signal field frequency and the idler field frequency to be changed. The system also includes an output unit for providing the first and second electromagnetic fields to the vibrational analysis equipment.

In accordance with another embodiment, the invention provides a system for providing a pump field at a first frequency and a Stokes electromagnetic field at a second frequency for a coherent anti-Stokes Raman scattering system. The system includes a non-linear crystal that may be pumped at a high repetition rate with a signal having a wavelength of between about 400 nm and about 700 nm to provide a pulsed signal field at a signal field frequency and a pulsed idler field at an idler field frequency as output. The signal field provides the pump field and the idler field provides the Stokes field. The system also includes a tuning system for adjusting a temperature of the non-linear crystal to change a difference between the signal field frequency and the idler field frequency such that the difference may provide Raman resonances from about 50 cm$^{-1}$ to about 3500 cm$^{-1}$.

In accordance with a further embodiment, the invention provides a method of providing a first electromagnetic field at a first frequency and a second electromagnetic field at a second frequency that is different than the first frequency to vibrational analysis equipment that is responsive to a difference between the first and second frequencies. The method includes the step of pumping a non-linear crystal at a high repetition rate to provide a pumped signal field at a signal field frequency and a pumped idler field at an idler field frequency as output. The signal field provides the first electromagnetic field and the idler field provides the second electromagnetic field. The method also includes the steps of providing the signal field and the idler field at a focal area, and tuning the signal field frequency and the idler field frequency such that a difference between the signal field frequency and the idler field frequency at the focal area is changed. The method further includes the step of providing the first and second electromagnetic fields to the vibrational analysis equipment.

BRIEF DESCRIPTION OF THE DRAWINGS

The following description may be further understood with reference to the accompanying drawings in which.

DETAILED DESCRIPTION OF THE ILLUSTRATED EMBODIMENTS

In accordance with certain embodiments, the invention provides a tunable picosecond dual frequency near infrared optical parametric oscillator (OPO) for noninvasive coherent anti-Stokes Raman scattering microscopy.

The OPO is a passive device that uses a non-linear crystal to convert the frequency of photons into signal and idler fields. In an OPO device, the photon energy of each pump photon splits into two photons of lower frequencies. One or two of those frequencies may then be made to resonate to enhance the power. Total energy, however, is conserved so that the pump photon energy equals the signal photon energy and the idler photon energy. The invention provides a laser source that includes a synchronously pumped OPO in which the two beams being produced by the laser are used in the Raman process (signal and idler for pump and Stokes) in accordance with an embodiment. Applicants have found that a laser wavelength of 532 nm is appropriate in certain embodiments to cover Raman resonances within a desired range. The system may then tune the laser near the intermediate point where Raman frequencies may be covered from wavelengths of a few hundred cm$^{-1}$ to few thousand cm$^{-1}$.

In certain embodiments, the invention provides a compact laser source that is based on a novel picosecond OPO for high performance CARS microscopy. The stable operation, non-invasiveness, broad tunability over the entire Raman frequencies region with a single nonlinear crystal, and improved penetration depth make it an optimal source for CARS imaging in chemical and biomedical research. The crystal may be pumped at a frequency in the visible range (about 400 nm to about 700 nm). The laser source may operate in the 900 nm and 1300 nm range, which is important for non-invasive imaging. Tunable two wavelength outputs of the OPO have been used that allows continuous coverage of the Raman resonances from 50 cm$^{-1}$ to 3500 cm$^{-1}$. The longer wavelengths may result in reduced photo-damage of biological samples at near-infrared pump and Stokes wavelengths, and higher penetration depths for CARS imaging due to reduced light scattering at the near-infrared wavelengths.

In accordance with an embodiment, a laser source for CARS microscopy is provided in which a broadly tunable picosecond OPO based on a periodically poled potassium titanyl phosphate (PP-KTP) crystal is synchronously pumped by the second harmonic (at 532 nm) output of a mode-locked Nd:YVO$_4$ laser. The OPO is continuously temperature tunable from its nearly degenerate point (1064 nm) to 890 nm for its signal beam and to 1325 nm for its idler beam. The system provides, in an embodiment, pulses such as 3-5 ps pulses generated an 80 MHz repetition rate. In further embodiments, the repetition rate may be range from about 1 MHz to about 1 GHz depending on the pump source characteristics for the wavelength being used, e.g., 532 nm. By using the signal and idler beams from the OPO as pump and Stokes beams for CARS, respectively, it is possible to cover the entire chemically important vibrational frequency range of 100 cm$^{-1}$-3700 cm$^{-1}$. With this new system, CARS imaging with sub-wavelength resolution in chemical and biological systems may be achieved. High penetration depths in tissue imaging may also be obtained due to the longer pump and Stokes wavelengths than those used in the existing systems.

Figure 1:
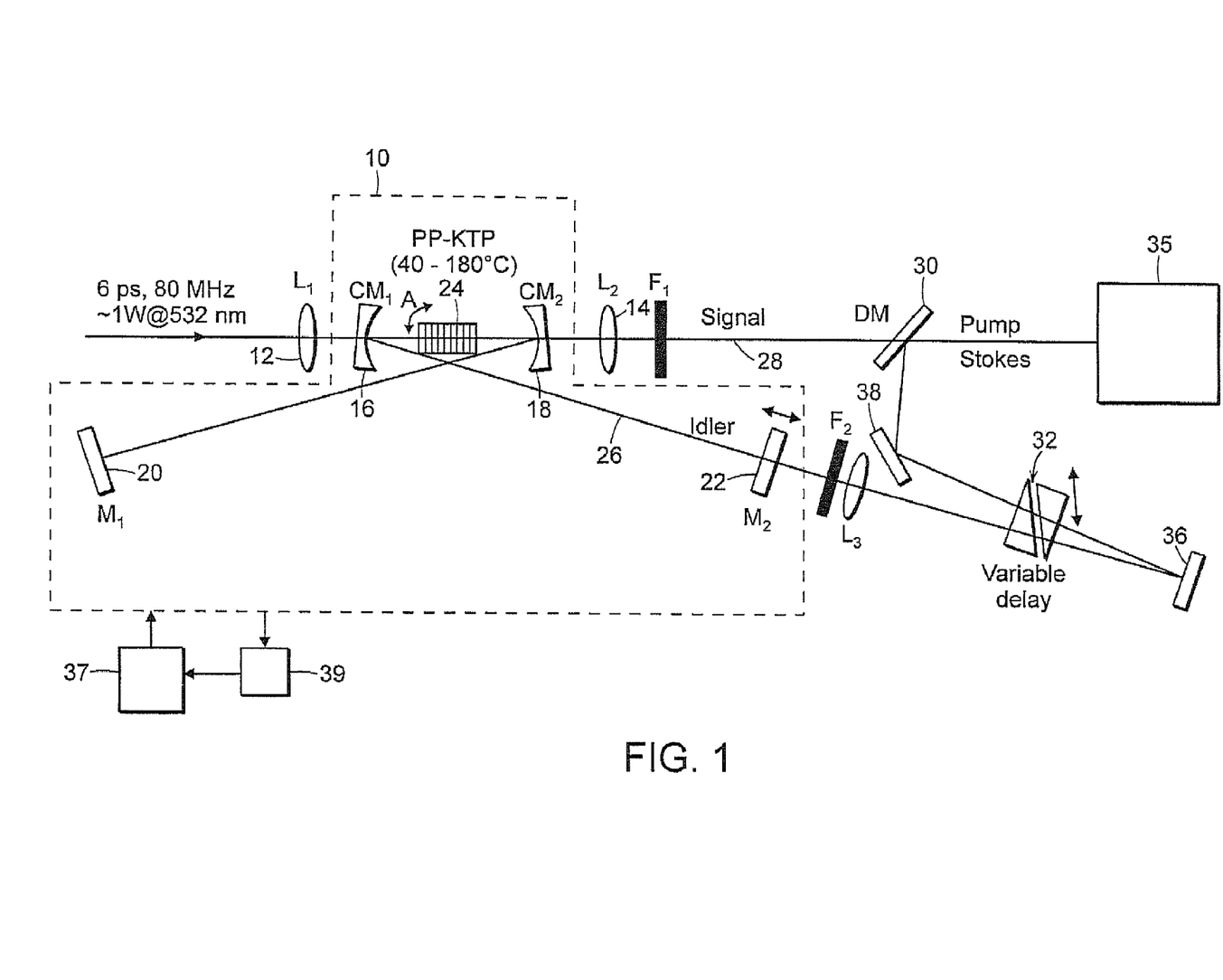
FIG. 1 shows an illustrative diagrammatic view of a system in accordance with an embodiment of the invention.

FIG. 1 shows a system in accordance with an embodiment of the invention in which the OPO resonator 10 is resonating within the idler beam wavelength range of about 1100 nm to about 1350 nm. The OPO design includes focusing lenses 12 and 14, concave mirrors 16 and 18, mirrors 20 and 22 and a crystal 24. The pump lens $L_1$ is −532 nm and has f=50 mm. The $CM_{1,2}$ concave mirrors are r=100 mm mirrors with high reflection (R>99%) in the idler beam wavelength range. The $CM_2$ mirror has 70-80% transmission at the signal beam wavelengths (about 850 m to about 1020 nm). The $M_1$ mirror 20 is a high reflecting mirror and the $M_2$ mirror 22 is 10% output coupler for the idler beam. The idler beam 26 is used to provide the Stokes beam and the signal 28 beam provides the pump beam. The system also includes a dichroic mirror 30, a variable delay unit 32, a lens 34 and mirrors 36 and 38. The two beams are out-coupled from the crystal so that they are co-propagating beams and share tailorable divergencies set by the operating conditions of the OPO. The pump and Stokes beams are provided to a CARS microscope or spectrascope 35 via conventional optics and/or an optical fiber. The detection of the anti-Stokes signal in the microscope may be in either the forward direction or the epi-direction as disclosed in U.S. Pat. No. 6,809,814. As discussed in more detail below, the system may be tuned by either adjusting the temperature of the resonator 10 using a heat source 37 and feedback unit 39, or may be tuned by rotating the crystal 24 with respect to the optical beam path axis as shown at A in FIG. 1.

Six picosecond pulses at 532 nm and an 80 MHz repetition rate were delivered by a frequency doubled, passively mode-locked Nd:$YVO_4$ Hi-Q laser. The maximum available average power of the laser (5 W) was reduced by an external variable attenuator. The OPO gain material is a flux-grown $KTiOPO_4$ crystal, 0.5×2.8×10.8 $mm^3$ (T×H×L), Z-cut and poled with a single grating period of Λ=8.99 μm, satisfying the first order phase-matching condition for second harmonic generation at about 41° C. The PP-KTP crystal was antireflection coated at the target wavelength of 1064 nm (R<0.2%) with a residual reflection of up to 1% at about 1300 nm. The length of the crystal is slightly above the temporal walk-off interaction length between the 6 ps pump and idler pulses. Very low pumping thresholds of less than 1 mW near degeneracy point of the tuning curve (doubly resonant operation) and about 40 mW for 924 nm/1254 nm signal/idler wavelengths were found. The temperature of the crystal may be changed by electrical induction or fluidic heating in a thermostatic controlled environment using for example, a heat source 37 and sensor 39 coupled to the resonator 10. In further embodiments, the system may be tuned by rotating the crystal 24 with respect to the optical axis as shown at A in FIG. 1.

Figure 2A:
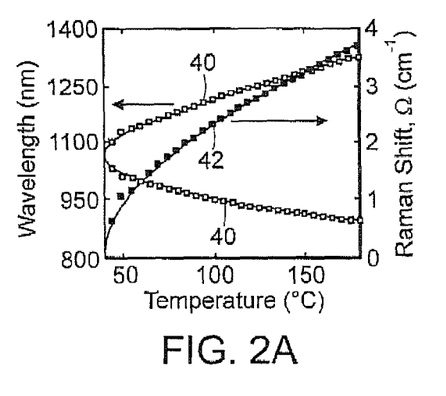
FIGS. 2A-2D show illustrative graphical views of wavelength tuning, power transfer, signal pulse power spectrum and autocorrelation trace respectively for a system in accordance with an embodiment of the invention.

FIG. 2A shows experimental wavelength tuning results as a function of temperature for the PP-KTP crystal at 40 (in the open circles), and shows the calculated theoretical values at 40 in the solid line based on the KTP material refractive index data. FIG. 2A also shows the corresponding accessible Raman frequencies as a function of temperature at 42 (in the closed circles) and shows the calculated theoretical values at 42 in the solid line. At the maximum set crystal temperature of 180° C., the corresponding OPO signal (pump) and idler (Stokes) pair of wavelengths are 889.4 nm and 1323.9 nm respectively, corresponding to a Raman shift of 3690 $cm^{-1}$.

Figure 2B:
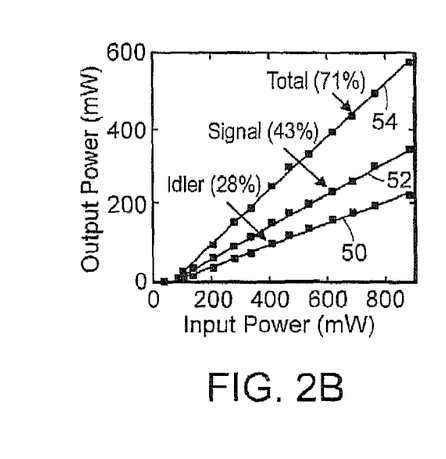

FIG. 2B shows output OPO power as a function of input power at the entrance of the crystal with the temperature T=132° C. The output power for the idler is shown at 50, the signal is shown at 52, and the total is shown at 54. The filled-in squares at 50, 52 and 54 represent measured power results, and the solid line is a linear fit for each.

The output signal, idler, and total power dependency versus the input pump power are shown at 50, 52 and 54 respectively in FIG. 2B when the OPO crystal is maintained at temperature 132° C. to deliver signal and idler beams at wavelengths of 921 nm and 1260 nm respectively. Linear slope efficiencies are observed for the signal, idler and total powers of 43%, 28% and 71% respectively up to the maximum pump power level. Output powers for both beams were fairly constant with about 10% to about 15% margin throughout the tuning range at fixed pump power.

Figure 2C:
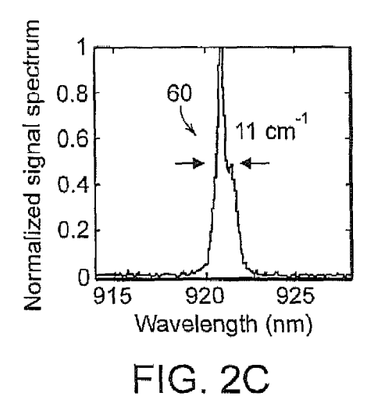
Figure 2D:
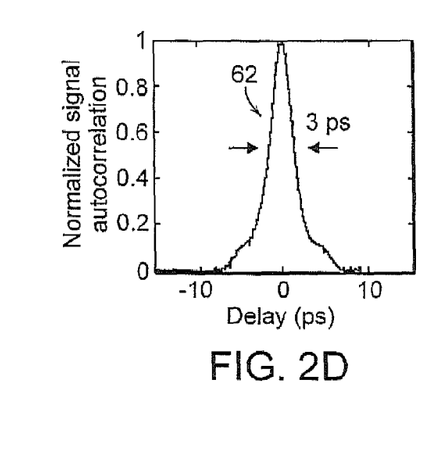

At maximum OPO output power, the OPO delivers pulses with a typical power spectrum of about 100 $cm^{-1}$ (FWHM) and pulse widths of about 7.5 ps. With the appropriate regime of group velocity mismatch and at certain parametric gain values, a variety of intensity profiles and spectra may be observed. For example, at an input pump power level of 715 mW and under a negative single pass cavity detuning of 36 μm, spectral narrowing down to about 11 $cm^{-1}$ occurs leading to less chirped pulse and tolerable pulse spectral bandwidth for resonant high contrast CARS imaging. As shown in FIG. 2C, the characteristic pulse power spectrum shows the spectral narrowing of the signal 60. As shown at 62 in FIG. 2D, the autocorrelation trace (function of delay time in picoseconds) at 132° C. for a negative single pass cavity detuning of 36 μm shows a shorter pulse. In fact, an approximately 2.5-times shorter signal pulse is observed as shown at 62 in FIG. 2D. The negative detuning resulted in 20% power drop from the maximum level. Therefore nearly optimal performance for CARS imaging purposes, and reliable long-term day-to-day operation at different crystal temperatures, is possible without any passive spectral filtering element in the cavity.

Signal and idler beams 26 and 28 respectively were out-coupled from the cavity as shown in FIG. 1. The idler pulse was delayed by the variable delay unit 32 and spatially combined with the signal on the dichroic mirror (DM) 30. The two beams were sent into a scanning microscope that makes use a 1.2 numerical aperture water immersion objective lens. Long pass filters ($F_{1,2}$) were used in order to block the OPO outputs at shorter (<850 nm) wavelengths due to several non-phase-matched nonlinear interactions in the PP-KTP crystal that take place. The two lenses ($L_{2,3}$, $f_2$=150 mm and $f_3$=1000 mm) in the beam paths were used to achieve optimal spot sizes for the beams at the objective lens entrance pupil. The total average power in the image plane of the microscope was attenuated to less than 20-30 mW. The two output beams at different frequencies are very suited for such microscopy given that they may have well correlated spatial and temporal characteristics.

In order to determine spatial resolution of the system, a series of resonant CARS image scans in samples with polystyrene beads of different sizes were performed by coherently exciting the CH aromatic band (about 2850 $cm^{-1}$), which is a major chemical bond of many live cell and tissue constituents. This experimental condition was achieved by choosing signal-idler pair of pulses at wavelengths of 924 nm and 1254 nm respectively. The characteristic lateral (x-y) resolution was determined to be about 420 nm while the longitudinal (z) resolution was about 1.1 μm, as expected from the diffraction limit.

Figure 3A:
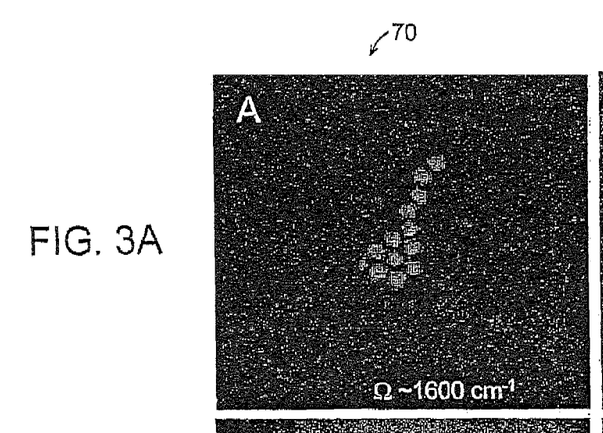
FIGS. 3A-3D show illustrative representations of CARS images of different subjects at different tuned wavelength from a system in accordance with an embodiment of the invention.
Figure 3B:
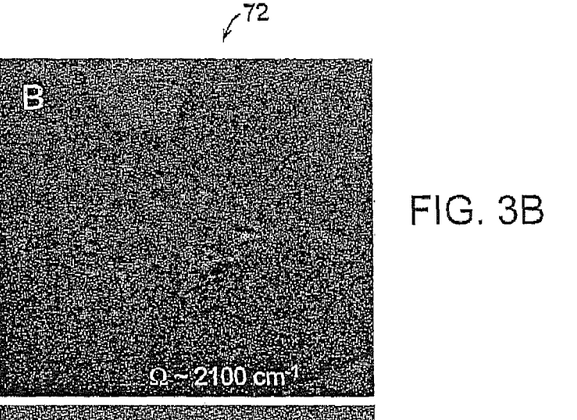
Figure 3C:
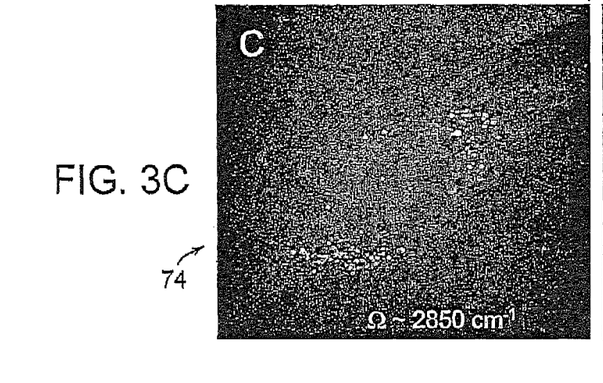
Figure 3D:
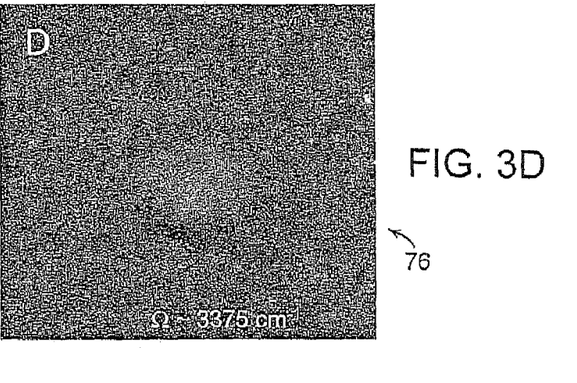

FIGS. 3A and 3B show CARS images across different Raman bands. FIG. 3A shows at 70 an image of a 1.5 micron diameter polystyrene bead cluster. The OPO wavelengths were tuned to target C=C stretching vibrational frequency, ($\omega_p$−$\omega_s$=1600 $cm^{-1}$). FIG. 3B shows at 72 a fibroblast cell NIH 3T3-L1 cultured with deuterium-labelled fatty acids, using C-D stretching vibration at $\omega_p-\omega_s=2100$ cm$^{-1}$ (due to the $CD_2$ groups replacing the $CH_2$ groups). The image size is 47 μm×47 μm. The strong signals arise from high density lipid structures. FIG. 3C shows at 74 the same cell type (NIH 3T3-L1) cultured in deuterium free media with C-H stretching vibration at $\omega_p-\omega_s=2850$ cm$^{-1}$ for $CH_2$. The image size is 78 μm×78 μm. FIG. 3D shows at 76 a 5-microns size POPS (1-palmitoyl-2-oleoyl-sn-glycero-3-phospho-L-serine) multilamellar vesicle image of lipids and water obtained via OH-stretching vibration at ($\omega_p-\omega_s=3375$ cm$^{-1}$) of the interlamellar water.

The system may, therefore, image highly heterogeneous tissue samples. It is known that the Rayleigh scattering cross-section for a media with sub-wavelength size features is inversely proportional to the fourth power of the wavelength. The longer pump and Stokes wavelengths, therefore, should increase the depth of penetration into tissue. With systems of the invention operating in the 900-1300 nm range, water absorption due to direct IR transitions is negligible. Higher penetration depths, however, may involve a reduction in spatial resolution.

Figure 4A:
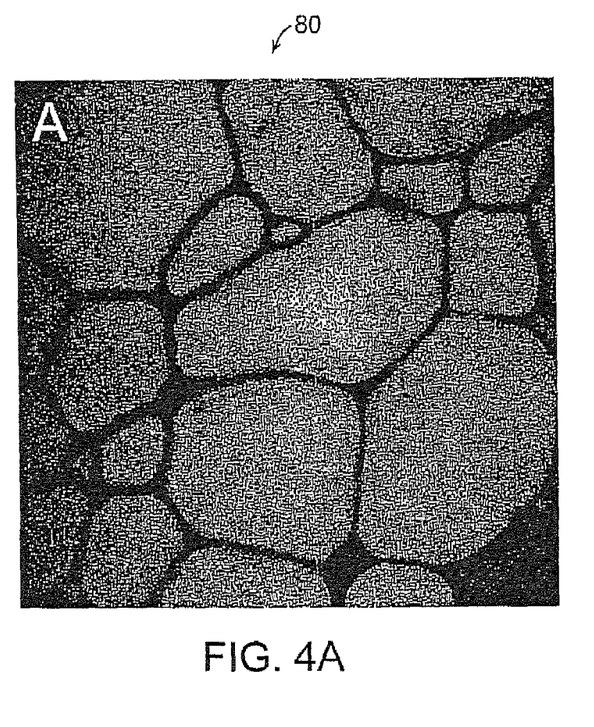
FIGS. 4A and 4B show illustrative representations of CARS images of lipid-structure rich tissue for two different samples from a system in accordance with an embodiment of the invention.
Figure 4B:
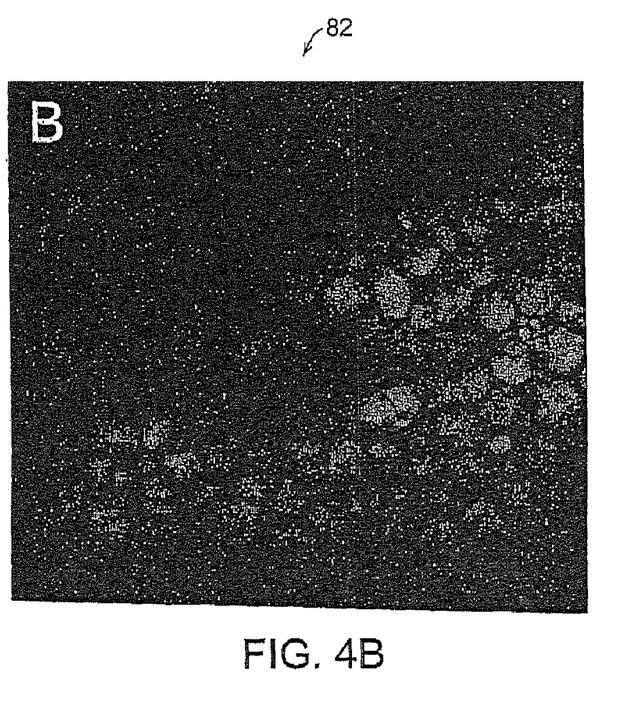

FIGS. 4A and 4B show forward propagating CARS-signal images of lipid-structure rich tissue at the aliphatic C-H stretching vibrational frequency of $\omega_p-\omega_s=2850$ cm$^{-1}$. FIG. 4A shows at 80 a subject white adipose tissue from the *omentum majus* of the mesenterium at a penetration depth of 10 microns. The image size is 117 μm×117 μm. This image demonstrates an example of high contrast resonant imaging of an unperturbed lipid rich tissue structures via C=H vibration resonances for the case of subject white adipose tissue from the *omentum majus* at fixed depth of 10 μm from the surface area. The corresponding set of wavelengths for pump, Stokes pulses for the OPO system are 924 nm, 1254 nm.

In contrast, for the same Raman shift, two synchronized Ti:sapphire lasers would typically have the wavelengths of 711 nm and 892 nm for the pump and Stokes beams. Such a system, however, would provide a much stronger scattering in the heterogeneous tissue. For example, a CARS image of ex-vivo tissue from a subject ear with the OPO and the electronically synchronized Ti:sapphire pulse trains is shown in FIG. 4B. In particular, FIG. 4B shows at 82 an ex-vivo subject ear tissue at a penetration depth from the skin of 130 μm by tuning into C=H stretching vibrational frequency using the OPO laser, exhibiting resonant features of lipid-rich adipocytes in the subcutaneous layer. No contrast is detected with pump and Stokes beams from the two electronically synchronized Ti:sapphire pulse trains. The OPO based laser system, however, allowed detection of resonant features positioned up to at least 70 microns deeper than the ones faintly seen by Ti:sapphire lasers based system.

At the excitation power employed above, no photodamage of any of the samples was observed. It is known that multiphoton processes induced by a mode-locked pulse train are primarily responsible for a sample's photodamage, which is significantly reduced at longer wavelengths. Systems in accordance with various embodiments of the invention, therefore, may be advantageous in reducing photodamage in CARS microscopy.

Near-infrared/infrared wavelength operation range of an OPO pumped by a visible laser source for a few examples is shown in Table 1 below. The frequency difference between the signal and idler beams is assumed to vary from about 100 cm$^{-1}$ to about 3700 cm$^{-1}$.

TABLE 1

| pump wavelength (nm) | signal and idler wavelength range (nm) |
|---|---|
| 400 | 697-939 |
| 500 | 844-1227 |
| 600 | 982-1542 |
| 700 | 1112-1889 |

Figure 5:
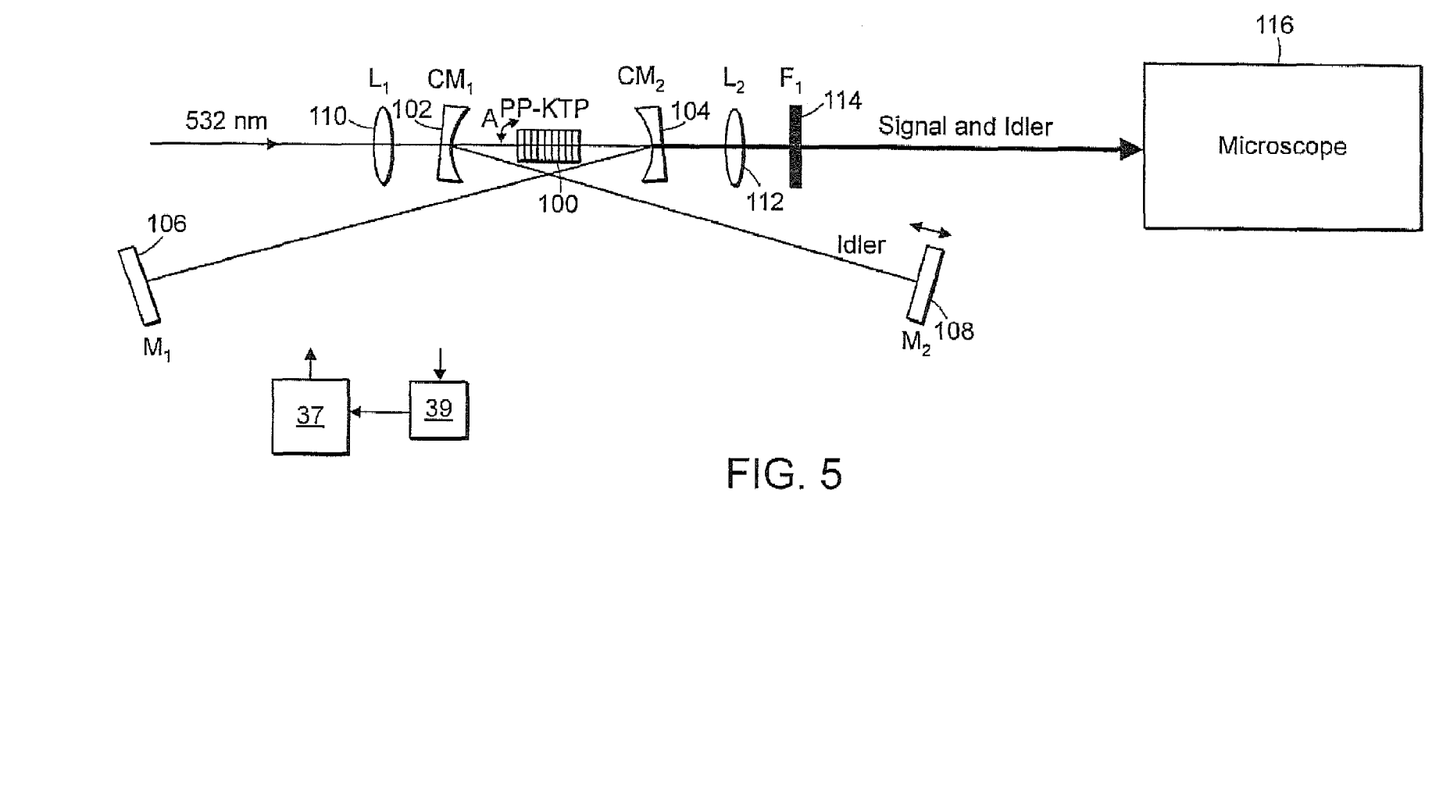
FIG. 5 shows an illustrative diagrammatic view of a system in accordance with another embodiment of the invention.

In accordance with another embodiment, the invention may provide a system that provides colinear pump and Stokes beams directly from the source itself. FIG. 5 shows a system in accordance with an embodiment of the invention that includes a crystal 100, concave mirrors 106 and 108, lenses 110 and 112, filter 114 and a microscope 116. Again, the system may be tuned by either adjusting the temperature of the resonator using a heat source and feedback unit, or may be tuned by rotating the crystal 100 with respect to the optical axis as discussed above with reference to FIG. 1. The elements may also be similar to those discussed above with reference to FIG. 1 except that the optical path of the idler beam must be accurately designed as its gross adjustability is not available in the system of FIG. 5. Moreover, the mirror 104 may be partially reflective as opposed to highly reflective as is mirror 14 in FIG. 1, and the mirror 108 may be highly reflective as opposed to being a partially reflecting output coupler as is mirror 22 of FIG. 1. The signal and idler beams provide the pump and Stokes beams respectively to a CARS microscope 116 via conventional optics and/or an optical fiber. Again, the detection of the anti-Stokes signal in the microscope may be in either the forward direction or the epi-direction as disclosed in U.S. Pat. No. 6,809,814.

Figure 6:
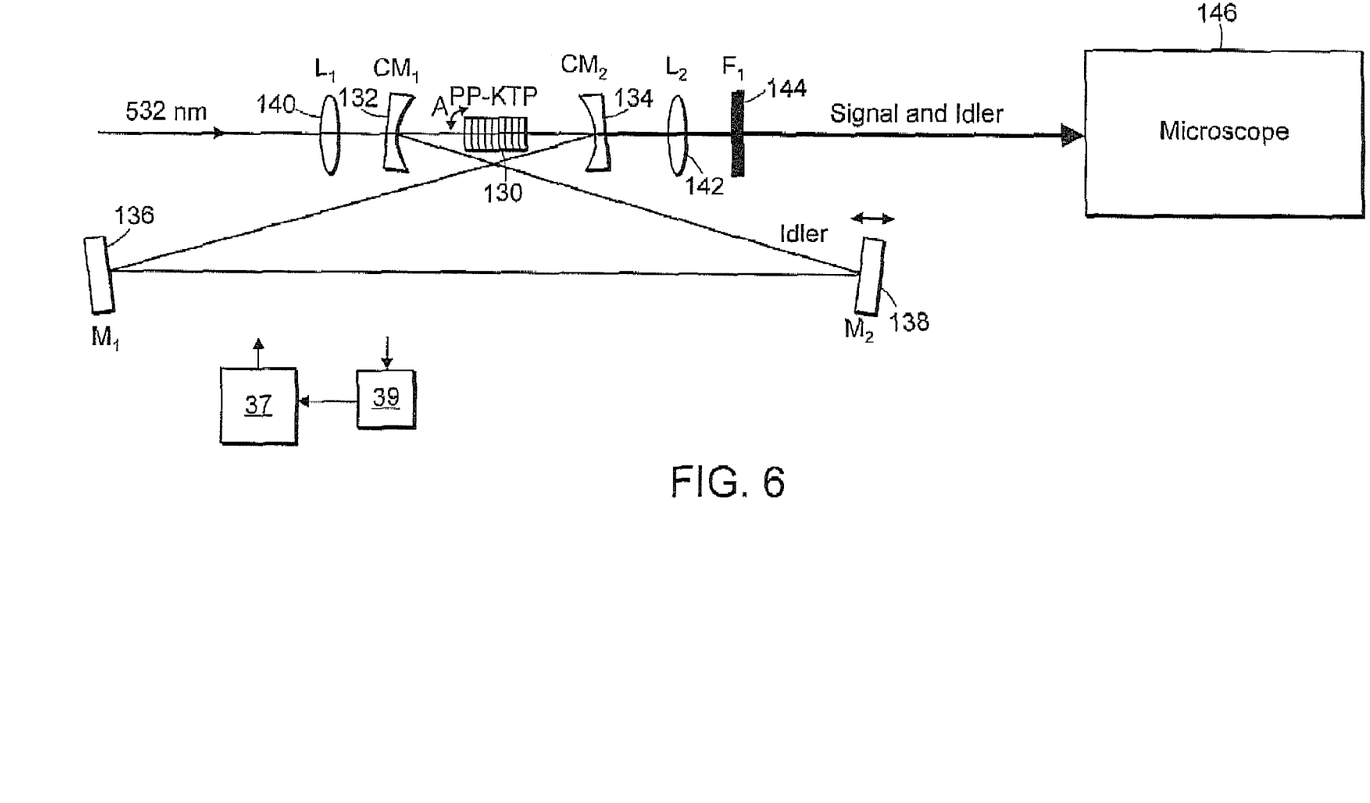
FIG. 6 shows an illustrative diagrammatic view of a system in accordance with a further embodiment of the invention.

In further embodiments, the resonator may include either a ring cavity configuration or a linear cavity configuration. The ring cavity configuration provides that low gain material may be used. The linear cavity configuration involves twice the losses as compared to the ring cavity configuration, and is therefore, better for high gain material. The tuning, may be achieved by adjusting the temperature to change the difference between the signal and idler frequencies, or may be achieved by changing angle of incidence of certain bi-refringent material, such as Lithium Niobate. For example, FIG. 6 shows a system similar to that shown in FIG. 5 in which the resonator is configured as a ring cavity configuration. In particular, the system of FIG. 6 includes a crystal 130, concave mirrors 132 and 134, mirrors 136 and 138, lenses 140 and 142, filter 144 and a microscope 146. Again, the system may be tuned by either adjusting the temperature of the resonator using a heat source and feedback unit, or may be tuned by rotating the crystal 130 with respect to the optical axis as discussed above with reference to FIG. 1. The elements may also be similar to those discussed above with reference to FIGS. 1 and 5 except that the optical path within the resonator now passes through the crystal less often prior to exiting the cavity. The signal and idler beams provide the pump and Stokes beams respectively to a CARS microscope 146 via conventional optics and/or an optical fiber. Again, the detection of the anti-Stokes signal in the microscope may be in either the forward direction or the epi-direction as disclosed in U.S. Pat. No. 6,809,814.

Figure 7:
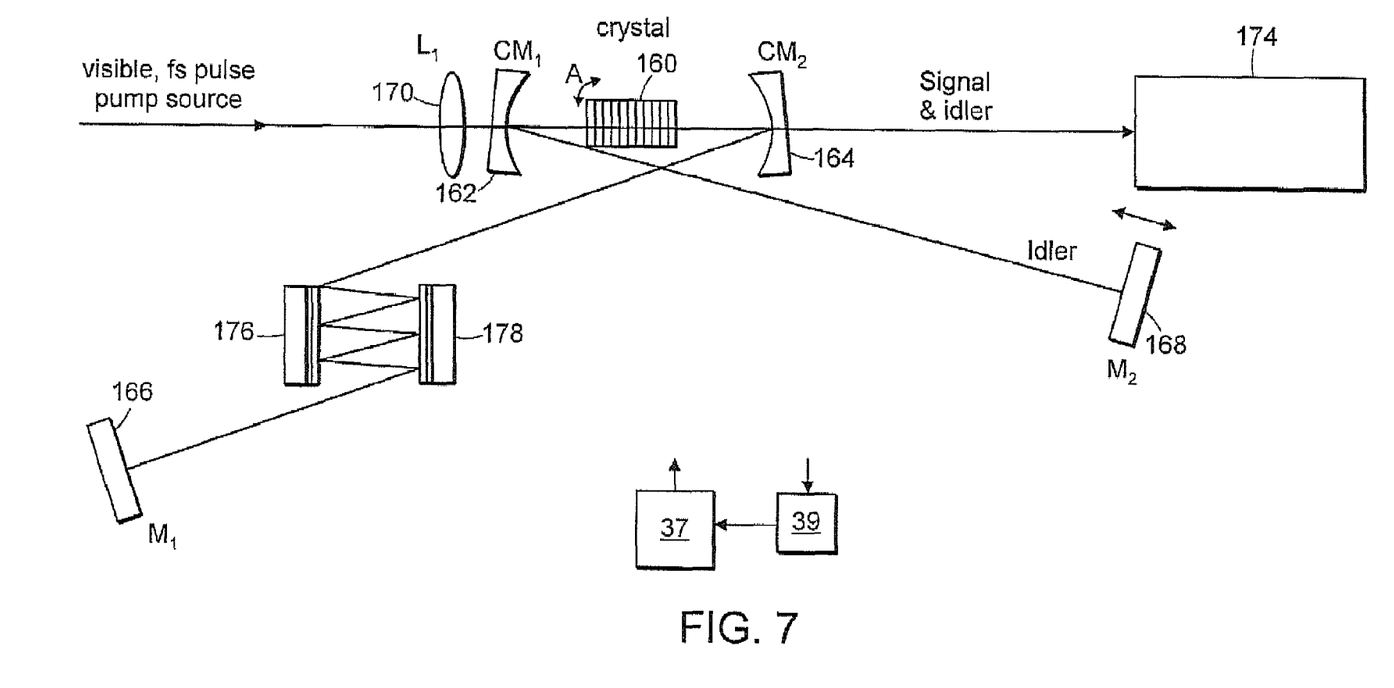
FIG. 7 shows an illustrative diagrammatic view of a system in accordance with a further embodiment of the invention.

Systems of the invention may also operate in with femtosecond pulses. In particular, either of the following configurations may provide tunable ultra-short pulses in a required wavelength range using synchronously pumped OPO pumped with femtosecond pulses in the visible range. For example, FIG. 7 shows a system that includes a crystal 160, concave mirrors 162 and 164, mirrors 166 and 168, lens 170, and a microscope 174. The system also includes a pair of chirped dielectric coated mirrors 176 and 178. Again, the system may be tuned by either adjusting the temperature of the resonator using a heat source and feedback unit, or may be tuned by rotating the crystal 130 with respect to the optical axis as discussed above with reference to FIG. 1. The elements may also be similar to those discussed above with reference to FIG. 1 except that the optical path within the linear resonator passes between the mirrors 176 and 178 many times in a single pass. The signal and idler beams provide the pump and Stokes beams respectively to a CARS microscope 174 via conventional optics and/or an optical fiber. Again, the detection of the anti-Stokes signal in the microscope may be in either the forward direction or the epi-direction as disclosed in U.S. Pat. No. 6,809,814.

Figure 8:
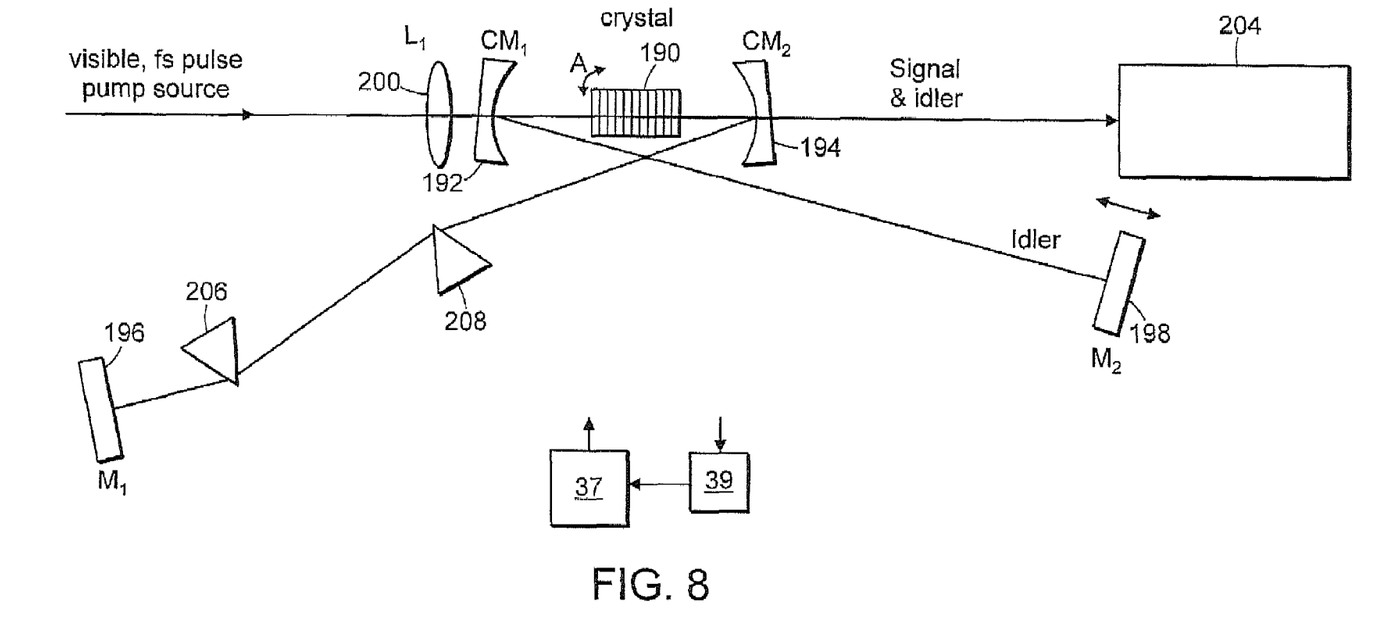
FIG. 8 shows an illustrative diagrammatic view of a system in accordance with a further embodiment of the invention.

FIG. 8 shows a system that includes a crystal 190, concave mirrors 192 and 194, mirrors 196 and 198, lens 200, and a microscope 204. The system also includes a pair of prisms 206 and 208. Again, the system may be tuned by either adjusting the temperature of the resonator using a heat source and feedback unit, or may be tuned by rotating the crystal 190 with respect to the optical axis as discussed above with reference to FIG. 1. The elements may also be similar to those discussed above with reference to FIG. 1 except that the optical path within the linear resonator passes between the through the prisms 206 and 208 each pass within the linear resonator. The signal and idler beams provide the pump and Stokes beams respectively to a CARS microscope 204 via conventional optics and/or an optical fiber. Again, the detection of the anti-Stokes signal in the microscope may be in either the forward direction or the epi-direction as disclosed in U.S. Pat. No. 6,809,814.

In the case of the cavity that utilizes prism pair, the distance between the pair and prism (FIG. 8) insertion depth into the beam is varied to achieve the shortest possible pulse. In the case of specially designed chirped dielectric coatings (FIG. 7) the number of beam bounces is a variable parameter. The crystal length is reduced to match temporal walk-off between visible pump and near-IR signal and idler pulses due to the group velocities mismatch (GVM) in the crystal.

Other types of crystals may also be used. For example, non-critically phase matched lithium triborate (LBO) crystal cut in X-Y plane (angle $\theta=90°$) may be used to provide an extremely wide range of wavelength tuning. By changing the temperature of the crystal, Raman frequencies may be obtained from a few hundred $cm^{-1}$ to a few thousand $cm^{-1}$. The entire tuning curve for the range of temperatures from 100 to 150 degrees C. may be achieved with such a crystal using a ring configuration. Although line widths of the pulse may be more than 20 $cm^{-1}$, the line width may be reduced by using a birefringent filter inside, so that the linewidth produced may be narrowed. With bulk characteristics, the advantage of the LBO is evident. For pump powers of as much as 4 Watts the crystal is stable and the contained external conversion efficiencies are more than 50%. This is contrary to KTP, which even though it has higher non-linearity and much lower threshold, it may not withstand power of 2 Watts: the crystal would be damaged. The maximum output power that may be realized is 500 mW (each beam is 250 mW).

The crystal therefore, may comprise for example 1) either bulk or periodically poled KTP crystal (potassium titanyl phosphate), 2) either bulk or periodically poled lithium niobate, 3) Magnesium oxide (MgO) doped periodically poled lithium niobate (PP-LNB(MgO)), 4) lithium triborate (LBO) crystal, 4) periodically poled lithium tantalate (PPLT), and 5) either bulk or periodically poled potassium tytanil arsenate (PP-KTA). Although the KTP may provide useful low power output ranges, the crystal may become too damaged at pump power levels of about 2000 mW. The LBO, on the other hand, has a higher threshold (about 1000 mW), but for higher power may be obtained (e.g., up to 3500 mW).

In certain embodiments, the signal and idler beams may be only 40 $cm^{-1}$ in difference from the bulk birefringently phase-matched KTP crystal ($\theta=90°$, $\phi=23°$). The auto-correlation trace width (FWHM) for the signal and idler beam may be from about 1 ps to about 6 ps. For certain applications, the guiding optics may separate co-propagating beams and then shape them so that they produce coinciding focal spots in the microscope. Telescopes may be used to provide optics processing to achieve this.

Those skilled in the art will appreciate that numerous further modifications and variations may be made to the above disclosed embodiments without departing from the spirit and scope of the invention.

The invention claimed is:

1. A system for providing a first electromagnetic field at a first frequency and a second electromagnetic field at a second frequency that is different than the first frequency to vibrational analysis equipment that is responsive to a difference between said first and second frequencies, said system comprising:
   a non-linear crystal that may be pumped at a high repetition rate to provide a picosecond pulsed signal field at a signal field frequency and a picosecond pulsed idler field at an idler field frequency as output, said signal field providing said first electromagnetic field and said idler field providing said second electromagnetic field, and wherein said pulsed signal field is collinear with said pulsed idler field upon exiting the system;
   tuning means for permitting the difference between said signal field frequency and said idler field frequency to be changed; and
   output means for providing the collinear first and second electromagnetic fields to the vibrational analysis equipment.

2. The system as claimed in claim 1 wherein said first electromagnetic field is used as a pump field in a coherent anti-Stokes Raman scattering (CARS) system, and said second electromagnetic field is used as a Stokes field in the CARS system.

3. The system as claimed in claim 1, wherein said non-linear crystal is pumped with a signal having a wavelength of between about 400 nm and about 700 nm.

4. The system as claimed in claim 1, wherein said non-linear crystal comprises at least one of potassium titanyl phosphate, lithium niobate, lithium triborate, and lithium tantalate.

5. The system as claimed in claim 1, wherein said non-liner crystal is a bulk material.

6. The system as claimed in claim 1, wherein said non-liner crystal is a periodically poled material.

7. The system as claimed in claim 1, wherein said tuning means includes means for changing the temperature of said non-liner crystal.

8. The system as claimed in claim 1, wherein said tuning means includes means for changing the angle of incidence of a pump field on the non-linear crystal.

9. The system as claimed in claim 1, wherein said system includes an optical parametric oscillator cavity.

10. A system for providing a pump field at a first frequency and a Stokes electromagnetic field at a second frequency for a coherent anti-Stokes Raman scattering system, said system comprising:

a non-liner crystal within a resonant cavity that may be pumped at a high repetition rate with a signal having a wavelength of between about 400 nm and about 700 nm to provide a pulsed signal field at a signal field frequency and a pulsed idler field at an idler field frequency as output, wherein the resonant cavity is defined by more than two mirrors, and wherein said pulsed signal field is collinear with said pulsed idler field upon exiting the resonant cavity, said signal field providing said pump field and said idler field providing said Stokes field; and tuning means for changing a difference between the signal field frequency and the idler field frequency such that the difference may provide Raman resonances from about 50 cm$^{-1}$ to about 3500 cm$^{-1}$.

11. The system as claimed in claim 10, wherein said non-linear crystal is pumped with a signal having a wavelength of 532 nm.

12. The system as claimed in claim 10, wherein said non-linear crystal comprises at least one of potassium titanyl phosphate, lithium niobate, lithium triborate, and lithium tantalate.

13. The system as claimed in claim 10, wherein said non-linear crystal is a bulk material.

14. The system as claimed in claim 10, wherein said non-linear crystal is a periodically poled material.

15. The system as claimed in claim 10, wherein said tuning means includes means for changing the angle of incidence of a pump field on the non-liner crystal.

16. The system as claimed in claim 10, wherein said system includes an optical parametric oscillator cavity.

17. The system as claimed in claim 10, wherein said system is coupled to a microscope for performing coherent anti-Stokes Raman scattering (CARS) microscopy.

18. The system as claimed in claim 17, wherein said system is coupled to said microscope via an optical fiber.

19. A method of providing a first electromagnetic field at a first frequency and a second electromagnetic field at a second frequency that is different than the first frequency to vibrational analysis equipment that is responsive to a difference between said first and second frequencies, said method comprising the steps of:

pumping a non-linear crystal within a laser ring cavity at a high repetition rate to provide a pumped signal field at a signal field frequency and a pumped idler field at an idler field frequency as output, said signal field providing said first electromagnetic field and said idler field providing said second electromagnetic field, wherein said pumped signal field is collinear with said pumped idler field upon exiting the laser ring cavity;

providing said collinear signal and idler fields at a focal area;

tuning said signal field frequency and said idler field frequency such that a difference between said signal field frequency and said idler field frequency at said focal area is changed; and providing a detected field from the focal area to the vibrational analysis equipment.

20. The method as claimed in claim 19 wherein said first electromagnetic field is used as a pump field in a coherent anti-Stokes Raman scattering (CARS) system, and said second electromagnetic field is used as a Stokes field in the CARS system.

21. The system as claimed in claim 1, wherein the collinear first and second electromagnetic fields are provided as 3-5 ps pulses generated at an 80 MHz repetition rate.

22. The system as claimed in claim 10, wherein said resonant cavity is defined by four minors.

23. The method as claimed in claim 19, wherein said method achieves high penetration depths of at least 10 microns in tissue imaging.

24. The method as claimed in claim 19, wherein said collinear signal and idler fields are provided at high repetition rates of at least 80 MHz.

* * * * *